US012724304B2

(12) United States Patent
Zhou et al.

(10) Patent No.: US 12,724,304 B2
(45) Date of Patent: Sep. 1, 2026

(54) LIQUID CRYSTAL DISPLAY DEVICE AND ONBOARD MONITORING DEVICE

(71) Applicant: WUHAN CHINA STAR OPTOELECTRONICS TECHNOLOGY CO., LTD., Wuhan (CN)

(72) Inventors: Yunhong Zhou, Wuhan (CN); Teng Wu, Wuhan (CN)

(73) Assignee: WUHAN CHINA STAR OPTOELECTRONICS TECHNOLOGY CO., LTD., Wuhan (CN)

( * ) Notice: Subject to any disclaimer, the term of this patent is extended or adjusted under 35 U.S.C. 154(b) by 371 days.

(21) Appl. No.: 18/552,903

(22) PCT Filed: Jun. 30, 2023

(86) PCT No.: PCT/CN2023/104700
§ 371 (c)(1),
(2) Date: Sep. 28, 2023

(87) PCT Pub. No.: WO2024/254917
PCT Pub. Date: Dec. 19, 2024

(65) Prior Publication Data

US 2025/0085585 A1 Mar. 13, 2025

(30) Foreign Application Priority Data

Jun. 15, 2023 (CN) ......................... 202310716995.0

(51) Int. Cl.

| | |
|---|---|
| ***G02F 1/1335*** | (2006.01) |
| ***A61B 5/00*** | (2006.01) |
| ***A61B 5/18*** | (2006.01) |

(52) U.S. Cl.
CPC ...... *G02F 1/133512* (2013.01); *A61B 5/0075* (2013.01); *A61B 5/18* (2013.01); *A61B 5/6893* (2013.01); *G02F 1/133514* (2013.01)

(58) Field of Classification Search
CPC ......... G02F 1/133512; G02F 1/133514; A61B 5/0075; A61B 5/18; A61B 5/6893
See application file for complete search history.

(56) References Cited

U.S. PATENT DOCUMENTS

| | | | | |
|---|---|---|---|---|
| 12,147,113 B2 * | 11/2024 | Wu | ........................ | G02F 1/1339 |
| 2019/0056622 A1 * | 2/2019 | Liu | .................. | G02F 1/136209 |

(Continued)

FOREIGN PATENT DOCUMENTS

| | | |
|---|---|---|
| CN | 108983468 A | 12/2018 |
| CN | 110071160 A | 7/2019 |

(Continued)

OTHER PUBLICATIONS

Cai et al, CN108983468A, machine translation Dec. 2018 (Year: 2018).*

(Continued)

*Primary Examiner* — Tracie Y Green
(74) *Attorney, Agent, or Firm* — PV IP PC; Peter Stecher; Wei Te Chung

(57) ABSTRACT

A liquid crystal display device comprises an infrared light-transmitting area, a light-shielding area, a backlight module, an infrared sensor, an infrared light-transmitting layer, and a first light-shielding layer, wherein the infrared sensor and the infrared light-transmitting layer are disposed in the infrared light-transmitting area, the infrared light-transmitting layer comprises a first color resist layer and a second color resist layer stacked and of different colors, the first light-shielding layer is disposed in the light-shielding area and comprises a first color resist light-shielding layer and a (Continued)

second color resist light-shielding layer stacked and of different colors.

12 Claims, 4 Drawing Sheets

(56) References Cited

U.S. PATENT DOCUMENTS

| | | | | |
|---|---|---|---|---|
| 2021/0055585 | A1* | 2/2021 | Yang | G02F 1/134309 |
| 2021/0223591 | A1* | 7/2021 | Zha | G02F 1/133519 |
| 2022/0092285 | A1* | 3/2022 | Tong | G02F 1/133514 |
| 2023/0367048 | A1* | 11/2023 | Zhang | G02B 5/201 |

FOREIGN PATENT DOCUMENTS

| | | | |
|---|---|---|---|
| CN | 110187546 | A | 8/2019 |
| CN | 110908164 | A | 3/2020 |
| CN | 112083600 | A | 12/2020 |
| CN | 113156692 | A | 7/2021 |
| CN | 113495378 | A | 10/2021 |
| CN | 113985645 | A | 1/2022 |
| KR | 20060027214 | A | 3/2006 |
| KR | 20120111394 | A | 10/2012 |
| WO | 2023082328 | A1 | 5/2023 |

OTHER PUBLICATIONS

Cn113985645a, machine translation, Jan. 2022 (Year: 2022).*

Lin, CN113156692A, machine translation Jul. 2021 (Year: 2021).*

Piao et al, CN110187546A, machine translation, Aug. 2018 (Year: 2018).*

International Search Report in International application No. PCT/CN2023/104700, mailed on Dec. 15, 2023.

Written Opinion of the International Search Authority in International application No. PCT/CN2023/104700, mailed on Dec. 15, 2023.

Chinese Office Action issued in corresponding Chinese Patent Application No. 202310716995.0 dated Jan. 22, 2025, pp. 1-8.

Chinese Office Action issued in corresponding Chinese Patent Application No. 202310716995.0 dated 03/28,2025, pp. 1-4.

* cited by examiner

LIQUID CRYSTAL DISPLAY DEVICE AND ONBOARD MONITORING DEVICE

CROSS-REFERENCE TO RELATED APPLICATIONS

This application is a national stage of International Application No. PCT/CN2023/104700, filed on Jun. 30, 2023, which claims priority to Chinese Application No. 202310716995.0, filed on Jun. 15, 2023, both of which are incorporated by reference herein.

TECHNICAL FIELD

The present application relates to the field of display technologies, and especially relates to a liquid crystal display device and an onboard monitoring device.

BACKGROUND

A driver monitor system (DMS) is primarily used for monitoring driver fatigue. With gradual development of technologies such as autonomous driving and internet of vehicles, the DMS has developed and iterated to include more functionalities. Considering protection of personal privacy, it is necessary to avoid direct collection of facial images in a visible light range. Moreover, a sensor is needed to be hidden.

Currently, an active infrared sensor is generally used for collecting information of infrared lights, thereby realizing functions such as monitoring the driving state and the like, to meet requirements of the driver monitor system. At the same time, the infrared sensor is integrated in a cluster module by referring to a camera under panel (CUP) technology widely applied to a mobile phone. As such, the sensor is hidden with a good integrated black effect.

However, the infrared lights have a certain lost in intensity with passing through a cover plate and a display panel to reach the infrared sensor under the display panel. As a result, imaging effect of the infrared sensor is affected. In the related art, a color resist layer, a black matrix, and a spacer layer disposed over an infrared sensor in a display panel are removed and replaced by a multi-layer stack of color resists with different colors. Meanwhile, a metal wiring is applied with a wire winding design to keep avoidance from the area for the infrared sensor, and the area needs to be blocked from lights by the black matrix. However, a new problem, where an integrated black effect of the display panel is affected due to a large difference in reflectivity of the display panel between the area for the infrared sensor and the area for the wire winding, which affects, is raised.

TECHNICAL PROBLEM

An embodiment of the present application provides a liquid crystal display device and an onboard monitoring device to solve a technical problem of a poor integrated black effect of an existing display device.

TECHNICAL SOLUTION

An embodiment of the present application provides a liquid crystal display device including an infrared light-transmitting area and a light-shielding area disposed outside the infrared light-transmitting area, the liquid crystal display device includes:

a first substrate and a second substrate oppositely disposed;

a backlight module disposed on a side of the first substrate away from the second substrate;

an infrared sensor disposed on a side of the backlight module away from the first substrate and disposed in the infrared light-transmitting area;

an infrared light-transmitting layer disposed between the second substrate and the first substrate and disposed in the infrared light-transmitting area, the infrared light-transmitting layer includes at least a first color resist layer 31 and a second color resist layer stacked and of different colors;

and a first light-shielding layer disposed between the second substrate and the first substrate and disposed in the light-shielding area;

wherein the first light-shielding layer includes a first color resist light-shielding layer and a second color resist light-shielding layer stacked and of different colors.

In some embodiments of the present application, the light-shielding area includes a first sub light-shielding area disposed around the infrared light-transmitting area, the liquid crystal display device includes a display area disposed around the first sub light-shielding area, and the first light-shielding layer is disposed in the first sub light-shielding area;

a metal winding section provided in the first sub light-shielding area and is arranged between the first substrate and the first shielding layer;

wherein an orthographic projection of the metal winding section on the first substrate is in an orthographic projection of the first light-shielding layer on the first substrate.

In some embodiments of the present application, the first light-shielding layer includes a third color resist light-shielding layer, wherein the first color resist light-shielding layer, the second color resist light-shielding layer, and the third color resist light-shielding layer are stacked and have different colors.

In some embodiments of the present application, material of two of the first color resist light-shielding layer, the second color resist light-shielding layer, and the third color resist light-shielding layer is same as material of the first color resist layer and the second color resist layer, respectively, and arranged in a same layer with the first color resist layer and the second color resist layer, wherein the first color resist light-shielding layer, the second color resist light-shielding layer, and the third color resist light-shielding layer are one of a red color resist layer, a green color resist layer, and a blue color resist layer, respectively.

In some embodiments of the present application, the infrared light-transmitting layer includes a third color resist layer, the first color resist layer, the second color resist layer, and the third color resist layer are stacked and have different colors, and a stacking sequence of the first color resist light-shielding layer, the second color resist light-shielding layer, and the third color resist light-shielding layer is based on a same color sequence as a stacking sequence of color resists of the first color resist layer, the second color resist layer, and the third color resist layer.

In some embodiments of the present application, the first color resist light-shielding layer, the second color resist light-shielding layer, and the third color resist light-shielding layer are stacked to define a first color resist stacked layers in an array, the first light-shielding layer includes a first black matrix block disposed between adjacent first color resist stacked layers.

In some embodiments of the present application, the first color resist light-shielding layer and the second color resist light-shielding layer define a first color resist stacked layer, the first light-shielding layer includes a first black matrix block disposed on a side of the first color resist stacked layer close to the first substrate and overlapped the first color resist stacked layer.

In some embodiments of the present application, the liquid crystal display device includes a display area between the infrared light-transmitting area and the first sub light-shielding area, a light filter layer between the second substrate and the first substrate, the light filter layer disposed in the display area, and a second black matrix block; wherein the light filter layer is disposed in the display area and includes a plurality of color resist blocks of varying colors, and the second black matrix block is disposed between adjacent color resist blocks.

In some embodiments of the present application, the liquid crystal display device includes a display area between the infrared light-transmitting area and the first sub light-shielding area, and a second light-shielding layer disposed between the second substrate and the first substrate; wherein the light-shielding area includes a second sub light-shielding area disposed around the display area, the second light-shielding layer disposed in the second sub light-shielding area, the second light-shielding layer includes a fourth color resist light-shielding layer, a fifth color resist light-shielding layer, and a sixth color resist light-shielding layer stacked and of different colors.

In some embodiments of the present application, the fourth, fifth and the sixth color resist light-shielding layers are stacked to define a second color resist stacked layer in an array, and the second light-shielding layer includes a third black matrix block disposed between adjacent second color resist stacked layers.

In some embodiments of the present application, the liquid crystal display device includes a display area between the infrared light-transmitting area and the first sub light-shielding area, and a second light-shielding layer disposed on a side of the second substrate and the first substrate; wherein the light-shielding area includes a second sub light-shielding area disposed around the display area, and the second light-shielding layer is disposed in the second sub light-shielding area; wherein the second light-shielding layer includes a fourth color resist light-shielding layer and a fifth color resist light-shielding layer stacked and of different colors, the fourth color resist light-shielding layer and the fifth color resist light-shielding layer define a second color resist layer, and the second light-shielding layer includes a third black matrix block disposed on a side of the second color resist layer close to the first substrate and overlapped with the second color resist layer.

In another aspect, the present application provides an onboard monitoring device including the liquid crystal display device of any one of the above embodiments.

BENEFICIAL EFFECT

The present application provides a liquid crystal display device and an onboard monitoring device including an infrared light-transmitting area and a light-shielding area disposed outside the infrared light-transmitting area, wherein the liquid crystal display device includes a first substrate and a second substrate oppositely disposed; a backlight module disposed on a side of the first substrate away from the second substrate, an infrared sensor disposed on a side of the backlight module away from the first substrate, an infrared light-transmitting layer disposed between the second substrate and the first substrate, and a first light-shielding layer, wherein the infrared sensor is located in the infrared light-transmitting area, the infrared light-transmitting layer is located in the infrared light-transmitting area. The infrared light-transmitting layer includes a first color resist layer and a second color resist layer stacked and of different colors. The first light-shielding layer is located in the light-shielding area, wherein the first light-shielding layer includes a first color resist light-shielding layer and a second color resist light-shielding layer stacked and of different colors, thereby the reflectivity difference between the light-shielding area and the infrared light-transmitting area is reduced, and the integrated black effect of the liquid crystal display device is improved.

DETAILED DESCRIPTION OF THE EMBODIMENTS

With reference to the drawings provided in the embodiments of this application, a clear and comprehensive description of the technical solutions in these embodiments is provided in the following. It should be understood that the described embodiments are only part of the examples of the present application, and not the entirety. Based on the embodiments in the present application, all other embodiments obtained by a person skilled in the art without involving any inventive effort are within the scope of the present application.

In the description of this application, it should be understood that the terms "first" and "second" are used for descriptive purposes only and are not to be construed as indicating or implying relative importance, or implying the number of indicated technical features. Therefore, features defined as "first" or "second" may explicitly or implicitly include one or more of the features. In the description of this application, "plurality" means two or more, unless expressly and specifically defined otherwise.

Currently, a driver monitor system (DMS) is mainly used for monitoring driver fatigue. A common method is to collect information of the infrared lights with band of 940±10 nm by an active infrared sensor, thereby realizing functions such as monitoring the driving state, to meet the requirements of the driver monitor system.

Figure 1:
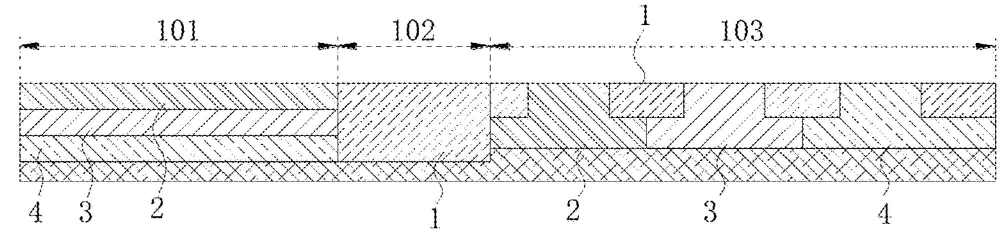
FIG. 1 is a partial schematic structure diagram of an exemplary liquid crystal display device.

Referring to FIG. 1, FIG. 1 is a partial schematic structure diagram of an exemplary display device.

In some embodiments, an onboard monitoring device includes a driver monitor system and a liquid crystal display device 100. The liquid crystal display device 100 includes a first substrate 10 and a second substrate 20 oppositely disposed, a liquid crystal layer sandwiched between the first substrate 10 and the second substrate 20, and a backlight module (not shown) disposed on a side of the first substrate 10 away from the second substrate 20. The liquid crystal display device 100 further includes an infrared light-transmitting area 101, a display area 103, and a first sub light-shielding area 102 between the infrared light-transmitting area 101 and the display area 103. The liquid crystal display device 100 further includes an infrared sensor (not shown) disposed on a side of the backlight module away from the first substrate 10, the backlight module includes a through hole corresponding to the infrared light-transmitting area 101, and the infrared sensor is disposed corresponding to the through hole. Since the lights with the infrared band of 940±10 nm have a low transmittance from the black matrix, the black matrix and the flatly arranged color resists of red, green, and blue in the infrared transparent area 101 are removed. A RGB stacked color resist of red color resist 2, green color resist 3, and blue color resist 4 is provided in the infrared transparent area 101 on a side of the second substrate 20 close to the first substrate 10. The lights with the infrared band of 940±10 nm have a high transmittance from the RGB stacked color filter, and the infrared sensor can be hidden by the RGB stacked color filter. Since the metal wiring in the infrared light-transmitting area 101 on a side of the first substrate 10 close to the second substrate 20 needs to be routed in the first sub light-shielding area 102 through the wire winding design, the black matrix is provided in the first sub light-shielding area 102 on a side of the second substrate 20 close to the first substrate 10 to block the metal wiring.

Figure 2:
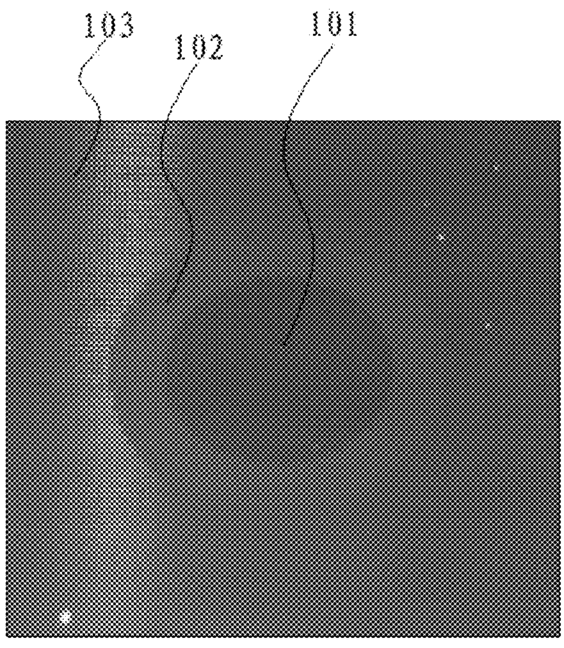
FIG. 2 is a partial diagram of reflectivity test results of the liquid crystal display device of FIG. 1.

As shown in FIG. 2, FIG. 2 is a photographed view to show the integrated black effect of the liquid crystal display device 100 of the above described design, wherein the liquid crystal display device 100 is turned off. It is found that the main reason for a poor integrated black effect of a turned off liquid crystal display device 100, and a brighter first sub light-shielding area 102 with respect to the infrared light-transmitting area 101, is that the reflectivity between the infrared light-transmitting area 101 and the first sub light-shielding area 102 in this design differs greatly.

Figure 3:
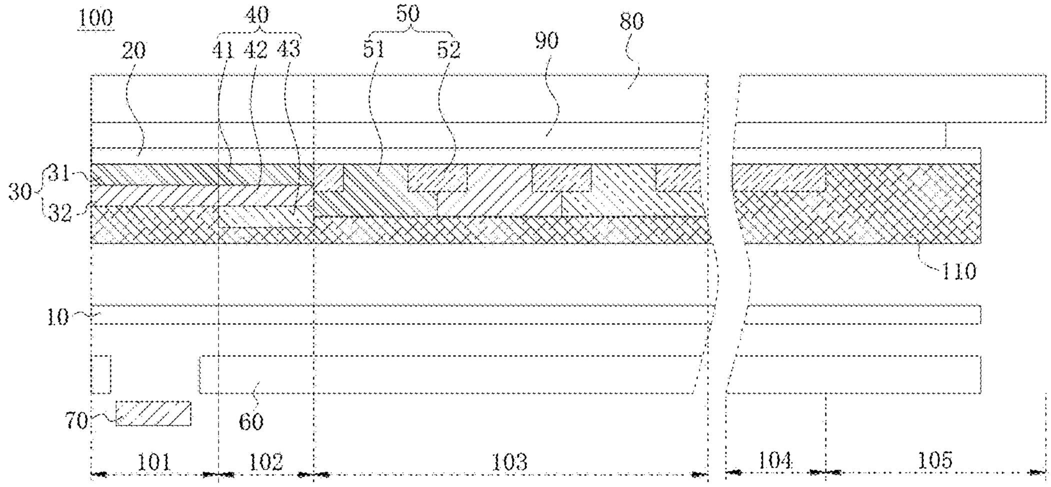
FIG. 3 is the first schematic structure diagram of a liquid crystal display device of an embodiment of the present application.
Figure 4:
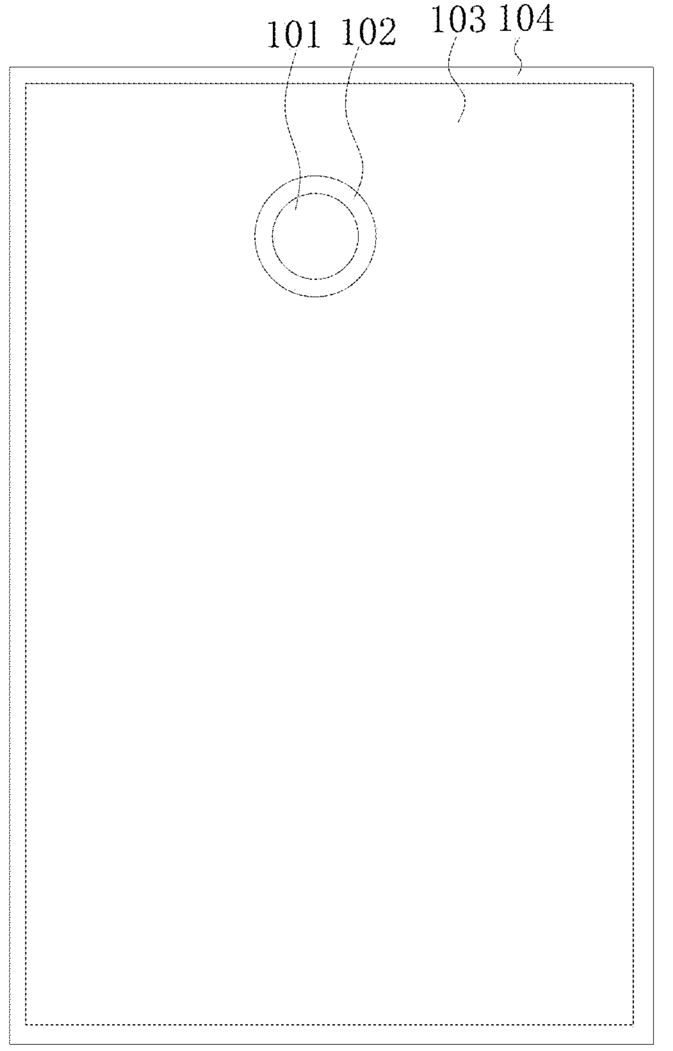
FIG. 4 is a schematic plan view of a liquid crystal display device of an embodiment of the present application.

Referring to FIGS. 3 and 4, an embodiment of the present application provides a liquid crystal display device 100.

The liquid crystal display device 100 includes an infrared light-transmitting area 101, and a light-shielding area SA located outside the infrared light-transmitting area 101. The infrared light-transmitting area 101 provides a high transmittance (greater than 90%) to the lights with the infrared band of 940±10 nm, and the light-shielding area SA is used to block the metal wiring to avoid the backlight module from light leakage. The liquid crystal display device 100 includes a first substrate 10 and a second substrate 20 oppositely disposed, a backlight module 60 disposed on a side of the first substrate 10 away from the second substrate 20, an infrared sensor 70 disposed on a side of the backlight module 60 away from the first substrate 10, an infrared light-transmitting layer 30 disposed between the second substrate 20 and the first substrate 10, and a first light-shielding layer 40 disposed between the second substrate 20 and the first substrate 10.

As shown in FIG. 3, in some embodiments, the first substrate 10 may be configured as an array substrate, and the second substrate 20 may be configured as a color film substrate. The infrared light-transmitting layer 30 and the first light-shielding layer 40 may be disposed on the second substrate 20, specifically may be disposed on a side of the second substrate 20 close to the first substrate 10. In some embodiments, the liquid crystal display device may be a display panel with color filter on array (COA, color films integrated on an array substrate). The infrared light-transmitting layer 30 and first light-shielding layer 40 may be provided on the first substrate 10, specifically may be provided on a side of the first substrate 10 close to the second substrate 20.

The infrared sensor 70 is disposed in the infrared light-transmitting area 101 for collecting information of infrared lights; the infrared light-transmitting layer 30 is located in the infrared light-transmitting area 101. The infrared light-transmitting layer 30 includes at least a first color resist layer 31 and a second color resist layer 32 stacked and of different colors. The infrared light-transmitting layer 30 provides a high transmittance and a low reflectance for the lights with the infrared band of 940±10 nm. The first light-shielding layer 40 is located in the light-shielding area SA and is used for shielding the metal wiring provided on the first substrate 10. The first light-shielding layer 40 includes a first color resist light-shielding layer and a second color resist light-shielding layer stacked and of different colors. Thus, a difference in reflectivity between the light-shielding area SA and the infrared light-transmitting area 101 is reduced, and the integrated black effect of the liquid crystal display device 100 is improved.

The technical solution of the present application is described in connection with specific examples.

Referring to FIG. 3, FIG. 3 is a first schematic structure diagram of a liquid crystal display device 100 of the present application.

The liquid crystal display device 100 of the present embodiment includes a first substrate 10 and a second substrate 20 oppositely disposed, a liquid crystal layer (not shown) disposed between the first substrate 10 and the second substrate 20, and a backlight module 60 disposed on a side of the first substrate 10 away from the second substrate 20. The backlight module 60 includes, but is not limited to, a backlight, a light guide plate, and an optical film. The first substrate 10 is provided with metal devices, such as array distributed pixel circuits and a plurality of signal lines, on the side close to the second substrate 20. The pixel circuits include, but are not limited to, elements of a transistor such as a gate electrode, an active layer, a source electrode, and a drain electrode. Details of this are not described in this embodiment, and reference may be made to conventional pixel circuits design.

The liquid crystal display device 100 includes an infrared sensor 70 disposed on a side of the backlight module 60 away from the first substrate 10, the infrared sensor 70 is configured for collecting information of the infrared lights of 940±10 nm band. The backlight module 60 is provided with an opening corresponding to the infrared sensor 70, and the opening exposes the infrared sensor 70.

Referring to FIG. 4, the liquid crystal display device 100 includes an infrared light-transmitting area 101, a display area 103, and a light-shielding area SA. The light-shielding area SA includes a first sub light-shielding area 102 between the infrared light-transmitting area 101 and the display area 103. The first sub light-shielding area 102 is disposed around the infrared light-transmitting area 101. The infrared light-transmitting area 101 and the first sub light-shielding area 102 do not function to display, but the display area 103 is used for display. An area of the display area 103 is much greater than an area of the infrared light-transmitting area 101 and an area of the first sub light-shielding area 102.

The infrared light-transmitting area 101 is shaped as, but not limited to, a rectangle, a square, or a circle. The present embodiment is described by using a circle as an example. The shape of the first sub light-shielding area 102 may be annular.

The liquid crystal display device 100 includes an infrared light-transmitting layer 30 and a first light-shielding layer 40 disposed on a side of the second substrate 20 close to the first substrate 10. The infrared sensor 70 and the infrared light-transmitting layer 30 are located in the infrared light-transmitting area 101. The infrared light-transmitting layer 30 has a lower transmittance for visible lights and a higher transmittance (greater than 90%) for the lights of infrared bands.

The first substrate 10 and the second substrate 20 include a rigid substrate or a flexible substrate, wherein the rigid substrate may be a transparent glass substrate, and the flexible substrate includes, but not limited to, a transparent polyimide substrate.

Figures 5, 6:
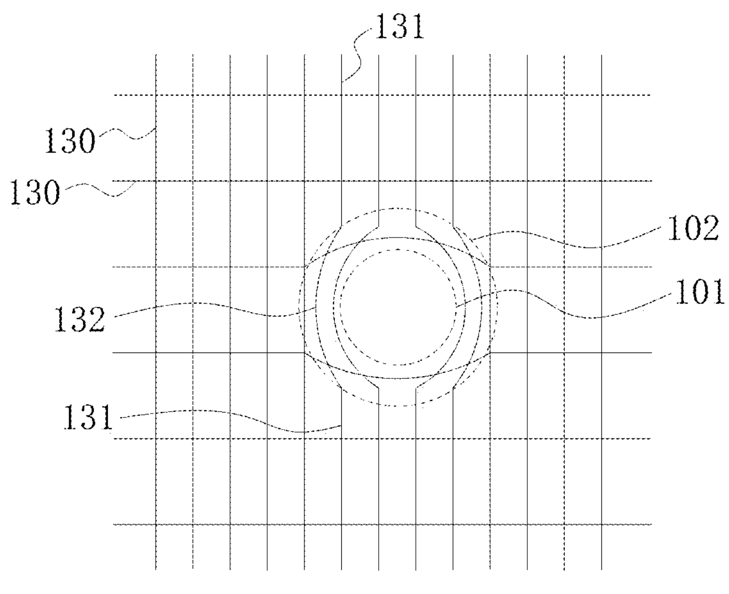
FIG. 5 is a partial schematic structure diagram of a part of a signal line of a liquid crystal display device of an embodiment of the present application.
FIG. 6 is a second schematic structure diagram of a liquid crystal display device of an embodiment of the present application.

As shown in FIG. 5, the first substrate 10 is provided with a plurality of signal lines 130 on the side close to the second substrate 20, and the signal line 130 includes but not limited to a gate line, a data line, a power line, and the like. The plurality of signal lines 130 are located outside the infrared light-transmitting area 101 to prevent the signal lines 130 from affecting the infrared sensor 70 to collect information of the infrared lights.

The display area 103 surrounds the infrared light-transmitting area 101, and the lights needs to be transmitted from the infrared light-transmitting area 101, so that the signal lines 130 need to be wound to circumvent the infrared light-transmitting area 101. Thus, the first sub light-shielding area 102 is designed for placing the metal winding section 132 of the signal line 130. However, the backlight module is provided under the metal winding section 132. Therefore, the first sub light-shielding area 102 needs to be effectively shielded to avoid light leakage of the backlight module.

The metal winding section 132 is disposed between the first substrate 10 and the first light-shielding layer 40, and an orthographic projection of the metal winding section 132 on the first substrate 10 is in an orthographic projection of the first light-shielding layer 40 on the first substrate 10.

Specifically, the plurality of signal lines 130 includes a metal winding section 132 and a metal straight line section 131, wherein the metal straight line section 131 is electrically connected to an end of the metal winding section 132, and the metal winding section 132 is located in the first sub light-shielding area 102. The shape of the metal winding section 132 includes, but is not limited to, an arc and a polyline, and the metal winding section 132 is disposed around at least a part of the infrared light-transmitting area 101. In a case that the infrared light-transmitting area 101 is circular, the metal winding section 132 is shape preferably as an arc; and in a case that the infrared light-transmitting area 101 is polygonal, such as square or rectangular, the metal winding section 132 is shaped preferably as a polyline.

In the present embodiment, the infrared light-transmitting layer 30 includes a first color resist layer 31 and a second color resist layer 32 that are stacked and of different colors.

The material of the first color resist layer 31 includes but not limited to one of the red color resist material, the green color resist material, and the blue color resist material. The material of the second color resist layer 32 includes but not limited to the other of the red color resist material, the green color resist material, and the blue color resist material. It should be understood that another color resist material, such as yellow color resist materials or the like, may be added or replace the above color resist material according to actual requirements.

Specifically, the infrared light-transmitting layer 30 includes a blue color resist layer and a red color resist layer stacked, or includes a red color resist layer and a green color resist layer stacked, or includes a blue color resist layer and a green color resist layer stacked.

The first light-shielding layer 40 includes a first color resist light-shielding layer 41, a second color resist light-shielding layer 42, and a third color resist light-shielding layer 43, which are stacked and have different colors. The material of two of the first color resist light-shielding layer 41, the second color resist light-shielding layer 42, and the third color resist light-shielding layer 43 is the same as the material of the first color resist layer 31 and the second color resist layer 32, respectively. The two of the first color resist light-shielding layer 41, the second color resist light-shielding layer 42, and the third color resist light-shielding layer 43 are disposed on a same layer as the first color resist layer 31 and the second color resist layer 32, respectively. Specifically, the first color resist light-shielding layer 41, the second color resist light-shielding layer 42, and the third color resist light-shielding layer 43 are a red color resist layer, a green color resist layer, and a blue color resist layer, respectively. Compared with the case in which the black matrix is used in the first sub light-shielding area for shielding the light, in the present embodiment, the red, green, and blue resist light-shielding layers are stacked to shield the lights. Therefore, not only the difference in reflectivity between the first sub light-shielding area 102 and the infrared light-transmitting area 101 can be reduced, but also an effective shielding effect can be achieved.

The stacking sequence of the first color resist light-shielding layer 41, the second color resist light-shielding layer 42, and the third color resist light-shielding layer 43 may not be limited. With the direction from the second substrate 20 towards the first substrate 10, the present embodiment takes the stacking sequence of the red color resist layer, green color resist layer, and blue color resist layer as examples for explanation.

The stacking sequence of the first color resist layer 31 and the second color resist layer 32 may be the same as or different from the stacking sequence of the color resist layers of the first light-shielding layer 40. Preferably, the stacking sequence is the same, so that the color resist layers of the same color of different areas can be formed by one patterning process, and the manufacture procedure can be saved.

The liquid crystal display device 100 includes a light filter layer 50 disposed on a side of the second substrate 20 close to the first substrate 10, and the light filter layer 50 includes a plurality of color resist blocks 51 of different colors. The color resist blocks 51 includes the red color resist block, the green color resist block, and the blue color resist block. A black matrix is provided between the adjacent color resist blocks 51 to prevent light leakage between the adjacent color resist blocks 51.

Referring to FIGS. 3 and 4, the liquid crystal display device 100 includes a second sub light-shielding area 104 surrounding the display area 103, and the second sub light-shielding area 104 is a frame area of the liquid crystal display device 100. A fan out wiring, a gate driving circuit, a source driving circuit, and the like are disposed on a side of the first substrate 10 of the second sub light-shielding area 104 close to the second substrate 20. The second substrate 20 is provided with a second light-shielding layer on a side close to the first substrate 10, and the second light-shielding layer may be a black matrix.

The black matrix of the present embodiment uses a material having a low reflectivity, and the black matrix has a reflectivity of less than 6.5%, specifically, may be 4.5%~5%. The reflectivity of the black matrix of the present embodiment can be reduced by 0.15%~0.2% compared to the reflectivity of the conventional black matrix (6.5%). Specifically, the material of the black matrix includes black porous titanium dioxide particles, and the black porous titanium dioxide particles have a high porosity to provide a better diffuse reflection effect for the lights. The reflectivity of the black matrix can be reduced by doping the black porous titanium dioxide particles. The material of the black matrix may further include at least one of the black pigment and the black dye, such as a black acrylic resin.

Referring to FIG. 3, since the film thicknesses of the infrared light-transmitting layer 30, the first light-shielding layer 40, and the second light-shielding layer provided on the second substrate 20 may be different, a planarization layer 110 is arranged on the sides of the infrared light-transmitting layer 30, the first light-shielding layer 40, and the second light-shielding layer away from the second substrate 20 to provide a flat surface for a subsequently formed film layer (such as a common electrode).

Referring to FIG. 6, FIG. 6 is a second schematic structure diagram of a liquid crystal display device of the present application.

The structure of the liquid crystal display device 100 in the present embodiment is similar to the first structure of the liquid crystal display device 100 provided in the above embodiment. Specifically, reference is made to the description of the first structure of the liquid crystal display device 100 in the above embodiment, and details are not described herein again. In the present embodiment, the infrared light-transmitting layer 30 includes a first color resist layer 31, a second color resist layer 32, and a third color resist layer 33.

Further, the stacking sequence of the first color resist light-shielding layer 41, the second color resist light-shielding layer 42, and the third color resist light-shielding layer 43 is based on a same color sequence as a stacking sequence of color resists of the first color resist layer 31, the second color resist layer 32, and the third color resist layer 33. Thus, the color resists of the same color may be formed by a same exposure process. In this embodiment, a stacking sequence of a red color resist, a green color resist, and a blue color resist is used as an example in the direction from the second substrate 20 toward the first substrate 10.

In the present embodiment, the technical solution of this embodiment is explained by an example where the display area 103, the infrared light-transmitting area 101, and the first sub light-shielding area 102 each have a red color resist with a film thickness of 2.24 microns, a green color resist with a film thickness of 2.18 microns, and a blue color resist with a film thickness of 2.46 microns.

Referring to Table 1 below, this embodiment tests the reflectivity of three areas of the liquid crystal display device 100 before and after the improvement, wherein the exemplary liquid crystal display device employs the structure of the display device of FIG. 1. The light source used for the test is a D65 standard light source, Y represents for reflectivity, and L represents for reflection luminance.

TABLE 1

| Exemplary liquid crystal display device | | | Liquid crystal display device of the present embodiment | | |
|---|---|---|---|---|---|
| Area | Y (D65) | $L^{*}$ (D65) | Area | Y (D65) | $L^{*}$ (D65) |
| Display area | 5.2% | 27 | Display area | 5.0%~5.05% | 26.5~27 |
| Light-shielding area | 5.8% | 29 | Light-shielding area | 4.9%~5.1% | 26~27 |
| Infrared light-transmitting area | 4.8% | 26 | Infrared light-transmitting area | 4.8% | 26 |

As can be seen from Table 1, the first light-shielding layer 40 of the first sub light-shielding area 102 of the present embodiment uses stacked red color resist layer, green color resist layer, and blue color resist layer. Compared with using a black matrix to shield the lights, the reflectivity of the first sub light-shielding layer decreases from 5.8% to 4.9%~5.1%, and the reflectivity of the first sub light-shielding layer is closer to the reflectivity of the infrared light-transmitting area 101, so that the integrated black effect of the liquid crystal display device can be effectively improved. In addition, the black matrix of the display area 103 of the present embodiment is made of a low reflectivity material. Compared with the conventional black matrix, the reflectivity of the display area 103 of the present embodiment is also reduced, and the reflectivity of the display area is closer to the infrared light-transmitting area 101, so that the integrated black effect of the liquid crystal display device is improved.

In the present embodiment, the transmittance of (the light having a wavelength band of 380~780 nm of) the light-shielding layer of the liquid crystal display device is measured before and after the improvement. The transmittance of the light-shielding layer of the liquid crystal display device is $1\times10^{-5.4}$ before the improvement, and after the improvement, the transmittance of the light-shielding layer of the liquid crystal display device is $8.07\times10^{-3}$ (obtained by multiplying the transmittance of red, green, and blue color resist layers, the transmittance of the red color resist layer is 0.171, the transmittance of the green color resist layer is 0.560, and the transmittance of the blue color resist layer is 0.084). Although the transmittance of the light-shielding layer of the improved liquid crystal display device increases somewhat, the influence on the light-shielding performance is negligible. Therefore, the liquid crystal display device of the present embodiment has a better integrated black effect, and the first sub light-shielding area 102 has a good shielding effect.

In the present application, the second light-shielding layer 120 of the second sub light-shielding area 104 includes a fourth color resist light-shielding layer 121, a fifth color resist light-shielding layer 122, and a sixth color resist light-shielding layer 123, which are stacked and have different colors. The fourth color resist light-shielding layer 121, the fifth color resist light-shielding layer 122, and the sixth color resist light-shielding layer 123 include the same material as the color resist block 51 of the display area 103. Specifically, the fourth color resist light-shielding layer 121 is one of a red color resist layer, a green color resist layer, and a blue color resist layer, and the fifth color resist light-shielding layer 122 and the sixth color resist light-shielding layer 123 are the other two of the red color resist layer, the green color resist layer, and the blue color resist layer, respectively.

Figure 7:
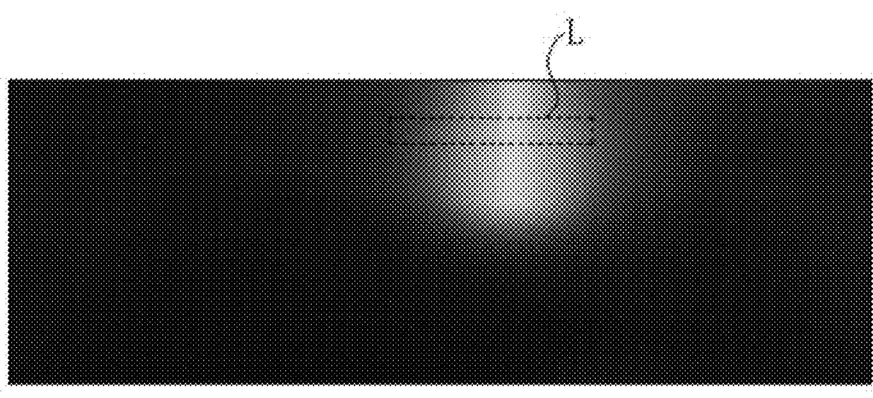
FIG. 7 is another partial diagram of reflectivity test results of an exemplary liquid crystal display device.

Referring to FIG. 7, FIG. 7 is a diagram showing an integrated black effect of a liquid crystal display device in a power off state when a black matrix structure is used for the second light-shielding layer of the second sub light-shielding area 104 in the exemplary art. As can be seen from FIG. 7, the lighting position presents a horizontal bright line L, which is located in the second light-shielding layer of the second sub light-shielding area 104, resulting in a high reflectivity. The reason is that the black matrix is used for shielding the light by the second light-shielding layer to lead a poor integrated black effect between the second sub light-shielding area 104 and the display area 103.

In this embodiment, the second light-shielding layer 120 is provided as a stack of the red color resistant layer, the green color resistant layer, and the blue color resistant layer, so that the difference in reflectivity between the second sub light-shielding area 104 and the display area 103 can be reduced, and the integrated black effect of the liquid crystal display device can be improved.

The second substrate 20 of this embodiment is provided with a cover plate 80 on the side away from the first substrate 10. The cover plate 80 is fully adhered to the second substrate 20 through an adhesive layer 90. The adhesive layer 90 may be selected OCA glue in smoky color or OCR glue in smoky color to increase the difference in reflectivity between the display area 103 and the second sub light-shielding area 104.

The cover plate 80 includes an ink area 105, and the second sub light-shielding area 104 is positioned between the display area 103 and the ink area 105. An ink layer is provided on a side of the cover plate 80 close to the second substrate 20, and the ink layer is located in the ink area 105. By adjusting the ink color and the transmittance of the ink layer, the reflection chromatic aberration between the ink area 105 and the display area 103 satisfies with $^{\Delta}E\leq 1$, thereby improving the integrated black effect of the liquid crystal display device.

Figure 8:
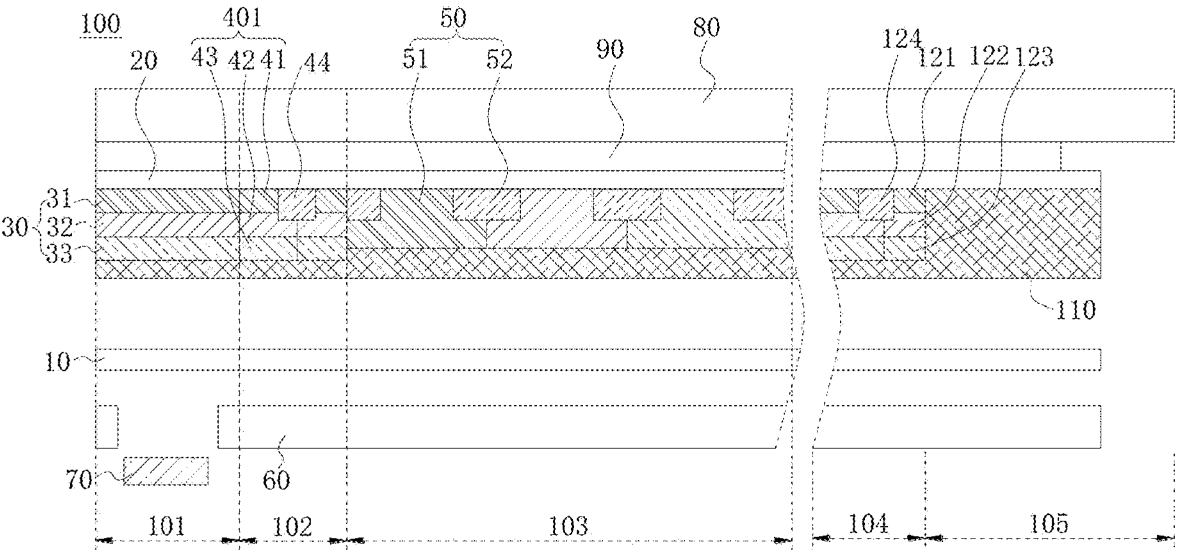
FIG. 8 is the third schematic structure diagram of a liquid crystal display device of an embodiment of the present application.

Referring to FIG. 8, FIG. 8 is a third schematic structure diagram of a liquid crystal display device of the present application.

The structure of the liquid crystal display device of the present embodiment is similar to the second structure of the liquid crystal display device of the above embodiment. For details, reference is made to the description of the liquid crystal display device of the above embodiment, therefore details are not described herein. In the present embodiment, a black matrix block is provided in the first light-shielding layer 40 and/or the second light-shielding layer 120.

As shown in FIG. 8, specifically, in the present embodiment, the first light-shielding layer 40 includes a first black matrix block 44. The first color resist light-shielding layer 41, second color resist light-shielding layer 42, and third color resist light-shielding layer 43 are stacked to define first color resist stacked layers in an array, and the first black matrix block 44 is disposed between adjacent first color resist stacked layers. By providing the first black matrix block 44 between adjacent first color resist stacked layers, the light-shielding performance of the first sub light-shielding area 102 can be improved while reducing the difference in reflectivity between the first sub light-shielding area 102 and the infrared light-transmitting area 101.

The metal wiring close to the display area in the first sub light-shielding area 102 is denser than the metal wiring close to the infrared light-transmitting area 101 in the first sub light-shielding area 102, and the area with a denser the metal wiring has a lower requirement on light-shielding. Therefore, the overall film thickness of the first light-shielding layer 40 close to the display area 103 in the first sub light-shielding area 102 may be less than the overall film thickness of the first light-shielding layer 40 close to the infrared light-transmitting area 101 in the first sub light-shielding area 102.

The liquid crystal display device includes a display area 103 located between the infrared light-transmitting area 101 and the first sub light-shielding area 102, and a light filter layer 50 disposed on the side of the second substrate 20 close to the first substrate 10. The light filter layer 50 is located in the display area 103. The light filter layer 50 includes a plurality of color resist blocks 51 of different colors, and a second black matrix block 52 located between adjacent color resist blocks 51.

In this embodiment, in the second sub light-shielding area 104, the fourth color resist light-shielding layer 121, the fifth color resist light-shielding layer 122, and the sixth color resist light-shielding layer 123 are stacked to define second color resist stacked layers in an array. The second light-shielding layer 120 includes a third black matrix block 124 disposed between adjacent second color resist stacked layers. As such, the shielding performance of the second sub light-shielding area 104 can be improved while reducing the difference in reflectivity between the second sub light-shielding area 104 and the display area 103.

Figure 9:
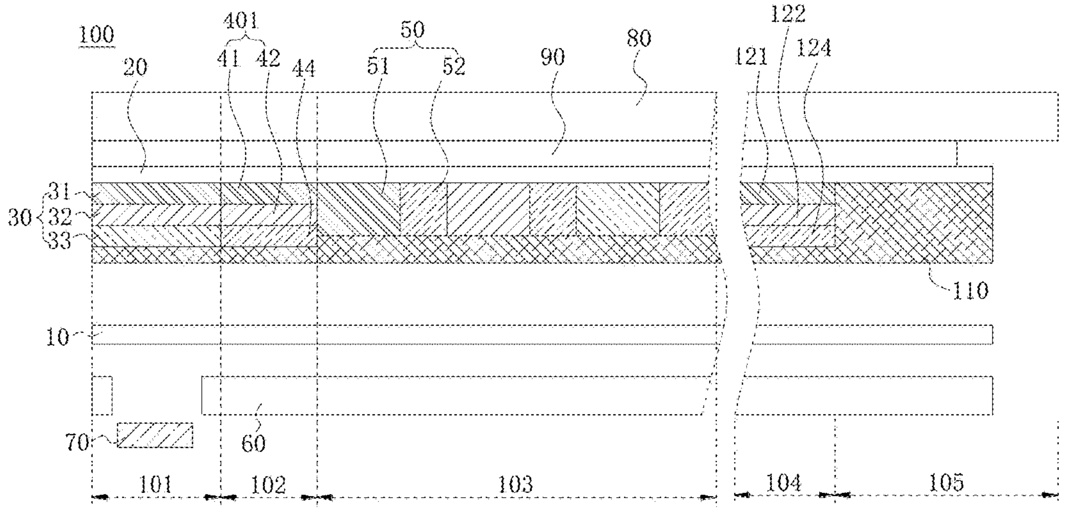
FIG. 9 is the fourth schematic structure diagram of a liquid crystal display device of an embodiment of the present application.

Referring to FIG. 9, FIG. 9 shows a fourth schematic structure diagram of a liquid crystal display device of the present application.

Compared with the third structure of the liquid crystal display device shown in FIG. 8, the first light-shielding layer 40 includes a first color resist light-shielding layer 41 and a second color resist light-shielding layer 42 stacked and of different colors. The first color resist light-shielding layer 41 and the second color resist light-shielding layer 42 define a first color resist stacked layer, and the first light-shielding layer 40 includes a first black matrix block 44. The first black matrix block 44 is disposed on the side of the first color resist stacked layer close to the first substrate 10 and overlapped with the first color resist stacked layer. The first color resist stacked layer may reduce the reflectivity of the first sub light-shielding area 102, but the first color resist stacked layer defined by two color resist light-shielding layers may cause the transmittance of the first sub light-shielding area 102 to rise. The first black matrix block 44 is provided under the first color resist stacked layer to reduce the transmittance of the light-shielding area.

Optionally, the material of the first color resist light-shielding layer 41 is the same as the material of the first color resist layer 31, and the material of the second color resist light-shielding layer 42 is the same as the material of the second color resist layer 32. The first color resist light-shielding layer 41 and the second color resist light-shielding layer 42 are each selected from a respective one of the red color resist layer, the green color resist layer, and the blue color resist layer. The color resists of the first color resist light-shielding layer 41 and the second color resist light-shielding layer 42 have different colors.

The transmittance of a stacked color resist layer defined by the red color resist and the blue color resist is lower than the transmittance of a stacked color resist layer defined by other color resists (such as by the red color resist and the green color resist, or the green color resist and the blue color resist), and therefore, the first color resist light-shielding layer 41 and the second color resist light-shielding layer 42 may be selected from the red color resist layer and the blue color resist layer, respectively. The color resists of the first color resist layer 31 and the second color resist layer 32 may not be limited in colors, and may be selected from any one of red, green, and blue color resist.

As shown in FIG. 9, the second sub light-shielding area 104 may also refer to the above described design. Specifically, the second light-shielding layer 120 includes a fourth color resist light-shielding layer 121 and a fifth color resist light-shielding layer 122 stacked and of different colors. The fourth color resist light-shielding layer 121 and the fifth color resist light-shielding layer 122 define a second color resist stacked layer. The second light-shielding layer 120 includes a third black matrix block 124 disposed on a side of the second color resist stacked layer close to the first substrate 10, and the third black matrix block 124 is overlapped with the second color resist stacked layer.

The material of the fourth color resist light-shielding layer 121 is the same as that of the first color resist layer 31, and the material of the fifth color resist light-shielding layer 122 is the same as that of the second color resist layer 32. The fifth color resist light-shielding layer 122 is selected from one of a red color resist layer, a green color resist layer, and a blue color resist layer, and the color resists of the fourth color resist light-shielding layer 121 and the fifth color resist light-shielding layer 122 have different colors.

The design principle of the second sub light-shielding area 104 is the same as that of the first sub light-shielding area 102, and details are not described herein.

The present application also provides an onboard monitoring device, and the onboard monitoring device includes the liquid crystal display device of any of the above embodiments, and a driver monitor system. The driver monitor system includes, but not limited to, a smoke monitoring unit, a telephone call monitoring unit, a distracted driving monitoring unit, an unfastened seat belt monitoring unit, a drinking monitoring unit, a yawning monitoring unit, a closed eye monitoring unit, and the like. The driver monitor system collects information of the infrared lights with the band of 940±10 nm based on the infrared photosensitive sensor, to implement a monitoring function.

As above, the present application provides a liquid crystal display device including an infrared light-transmitting area 101 and a light-shielding area SA located outside the infrared light-transmitting area 101. The liquid crystal display device includes a first substrate 10 and a second substrate 20 oppositely disposed, a backlight module 60 disposed on a side of the first substrate 10 away from the second substrate 20, an infrared sensor 70 disposed on a side of the backlight module 60 away from the first substrate 10, an infrared light-transmitting layer 30 disposed on a side of the second substrate 20 close to the first substrate 10, and a first light-shielding layer 40 disposed on a side of the second substrate 20 close to the first substrate 10. The infrared sensor 70 is located in the infrared light-transmitting area 101, and the infrared light-transmitting layer 30 is located in the infrared light-transmitting area 101. The infrared light-transmitting layer 30 includes at least a first color resist layer 31 and a second color resist layer 32 stacked and of different colors. The first light-shielding layer 40 is located in the light-shielding area SA, wherein the first light-shielding layer 40 includes a color resist stacked layer of the same material as the first color resist layer 31 and the second color resist layer 32. The difference in reflectivity between the light-shielding area SA and the infrared light-transmitting area 101 is reduced, and the integrated black effect of the liquid crystal display device is improved.

In the above mentioned embodiments, the description of each embodiment has its own emphasis, and parts not described in detail in a certain embodiment may be referred to the related description of other embodiments.

A liquid crystal display device and an onboard monitoring device of an embodiment of the present application are described in detail. Specific examples are used to describe the principles and embodiments of the present application. The description of the above embodiment is merely intended to help understand the technical solution and the core idea of the present application. Those skilled in the art should understand that modifications may still be made to the technical solutions described in the foregoing embodiments, or equivalents may be made to some of the technical features therein; and these modifications or replacements do not depart the essence of the corresponding technical solutions from the scope of the technical solutions of the embodiments of the present application.

The invention claimed is:

1. A liquid crystal display device, comprising an infrared light-transmitting area, and a light-shielding area outside the infrared light-transmitting area, wherein the liquid crystal display device comprises:

a first substrate and a second substrate oppositely disposed;

a backlight module disposed on a side of the first substrate away from the second substrate;

an infrared sensor disposed on a side of the backlight module away from the first substrate, and disposed in the infrared light-transmitting area;

an infrared light-transmitting layer disposed between the second substrate and the first substrate, and disposed in the infrared light-transmitting area, wherein the infrared light-transmitting layer comprises a first color resist layer, a second color resist layer and a third color resist layer, wherein the first color resist layer, the second color resist layer and the third color resist layer are stacked and have different colors; and a first light-shielding layer disposed between the second substrate and the first substrate, and disposed in the light-shielding area;

wherein the first light-shielding layer comprises a first color resist light-shielding layer, a second color resist light-shielding layer and a third color resist light-shielding layer, wherein the first color resist light-shielding layer, the second color resist light-shielding layer, and the third color resist light-shielding layer are stacked and have different colors; a stacking sequence of the first color resist light-shielding layer, the second color resist light-shielding layer, and the third color resist light-shielding layer is based on a same color sequence as a stacking sequence of color resists of the first color resist layer, the second color resist layer, and the third color resist layer, wherein the first color resist light-shielding layer, the second color resist light-shielding layer, and the third color resist light-shielding layer are stacked to define first color resist stacked layers, and the first light-shielding layer comprises a first black matrix block disposed between adjacent first color resist stacked layers.

2. The liquid crystal display device of claim 1, wherein the light-shielding area comprises a first sub light-shielding area disposed around the infrared light-transmitting area, the liquid crystal display device comprises a display area disposed around the first sub light-shielding area, and the first light-shielding layer is disposed in the first sub light-shielding area;

wherein a metal winding section is provided in the first sub light-shielding area and is arranged between the first substrate and the first light-shielding layer; and an orthographic projection of the metal winding section on the first substrate is in an orthographic projection of the first light-shielding layer on the first substrate.

3. The liquid crystal display device of claim 2, wherein the first color resist light-shielding layer and the second color resist light-shielding layer define a first color resist stacked layer, and the first light-shielding layer comprises a first black matrix block disposed on a side of the first color resist stacked layer close to the first substrate and overlapped with the first color resist stacked layer.

4. The liquid crystal display device of claim 3, wherein the liquid crystal display device comprises a display area between the infrared light-transmitting area and the first sub light-shielding area, a light filter layer between the second substrate and the first substrate, and a second black matrix block; wherein the light filter layer is disposed in the display area and comprises a plurality of color resist blocks of different colors, and the second black matrix block is disposed between adjacent color resist blocks.

5. The liquid crystal display device of claim 2, wherein the liquid crystal display device comprises a display area between the infrared light-transmitting area and the first sub light-shielding area, and a second light-shielding layer disposed between the second substrate and the first substrate; wherein the light-shielding area comprises a second sub light-shielding area disposed around the display area, the second light-shielding layer is disposed in the second sub light-shielding area, and the second light-shielding layer comprises a fourth color resist light-shielding layer, a fifth color resist light-shielding layer, and a sixth color resist light-shielding layer stacked and of different colors.

6. The liquid crystal display device of claim 5, wherein the fourth color resist light-shielding layer, fifth color resist light-shielding layer, and sixth color resist light-shielding layer are stacked to define second color resist stacked layers in an array, and the second light-shielding layer comprises a third black matrix block disposed between adjacent second color resist stacked layers.

7. The liquid crystal display device of claim 2, wherein the liquid crystal display device comprises a display area between the infrared light-transmitting area and the first sub light-shielding area, and a second light-shielding layer disposed on a side of the second substrate and the first substrate; wherein the light-shielding area comprises a second sub light-shielding area disposed around the display area, and the second light-shielding layer is disposed in the second sub light-shielding area; and wherein the second light-shielding layer comprises a fourth color resist light-shielding layer and a fifth color resist light-shielding layer stacked and of different colors, the fourth color resist light-shielding layer and the fifth color resist light-shielding layer define a second color resist layer, the second light-shielding layer comprises a third black matrix block disposed on a side of the second color resist layer close to the first substrate and overlapped with the second color resist layer.

8. An onboard monitoring device, comprising a liquid crystal display device including an infrared light-transmitting area and a light-shielding area outside the infrared light-transmitting area, wherein the liquid crystal display device comprises:

a first substrate and a second substrate oppositely disposed;

a backlight module disposed on a side of the first substrate away from the second substrate;

an infrared sensor disposed on a side of the backlight module away from the first substrate and disposed in the infrared light-transmitting area;

an infrared light-transmitting layer disposed between the second substrate and the first substrate and disposed in the infrared light-transmitting area, wherein the infrared light-transmitting layer comprises a first color resist layer, a second color resist layer and a third color resist layer, wherein the first color resist layer, the second color resist layer and the third color resist layer are stacked and have different colors; and a first light-shielding layer disposed between the second substrate and the first substrate and disposed in the light-shielding area;

wherein the first light-shielding layer comprises a first color resist light-shielding layer, a second color resist light-shielding layer and a third color resist light-shielding layer, wherein the first color resist light-shielding layer, the second color resist light-shielding layer, and the third color resist light-shielding layer are stacked and have different colors; a stacking sequence of the first color resist light-shielding layer, the second color resist light-shielding layer, and the third color resist light-shielding layer is based on a same color sequence as a stacking sequence of color resists of the first color resist layer, the second color resist layer, and the third color resist layer, wherein the first color resist light-shielding layer, the second color resist light-shielding layer, and the third color resist light-shielding layer are stacked to define first color resist stacked layers, and the first light-shielding layer comprises a first black matrix block disposed between adjacent first color resist stacked layers.

9. The onboard monitoring device of claim 8, wherein the light-shielding area comprises a first sub light-shielding area disposed around the infrared light-transmitting area, the liquid crystal display device comprises a display area disposed around the first sub light-shielding area, and the first light-shielding layer is disposed in the first sub light-shielding area;

wherein a metal winding section is provided in the first sub light-shielding area and is arranged between the first substrate and the first light-shielding layer;

an orthographic projection of the metal winding section on the first substrate is in an orthographic projection of the first light-shielding layer on the first substrate.

10. The onboard monitoring device of claim 9, wherein the first color resist light-shielding layer and the second color resist light-shielding layer define a first color resist stacked layer, and the first light-shielding layer comprises a first black matrix block disposed on a side of the first color resist stacked layer close to the first substrate and overlapped with the first color resist stacked layer.

11. The onboard monitoring device of claim 10, wherein the liquid crystal display device comprises a display area between the infrared light-transmitting area and the first sub light-shielding area, a light filter layer between the second substrate and the first substrate, and a second black matrix block; wherein the light filter layer is disposed in the display area and comprises a plurality of color resist blocks of different colors, and the second black matrix block is disposed between adjacent color resist blocks.

12. The onboard monitoring device of claim 9, wherein the liquid crystal display device comprises a display area between the infrared light-transmitting area and the first sub light-shielding area, and a second light-shielding layer disposed between the second substrate and the first substrate; wherein the light-shielding area comprises a second sub light-shielding area disposed around the display area, the second light-shielding layer is disposed in the second sub light-shielding area, and the second light-shielding layer comprises a fourth color resist light-shielding layer, a fifth color resist light-shielding layer, and a sixth color resist light-shielding layer stacked and of different colors.

* * * * *